United States Patent [19]
Kasid et al.

[11] Patent Number: 6,126,965
[45] Date of Patent: Oct. 3, 2000

[54] LIPOSOMES CONTAINING OLIGONUCLEOTIDES

[75] Inventors: Usha Kasid, Rockville, Md.; Prafulla Gokhale, McLean, Va.; Anatoly Dritschilo, Bethesda, Md.; Aquilur Rahman, Long Grove, Ill.

[73] Assignee: Georgetown University School of Medicine, Washington, D.C.

[21] Appl. No.: 08/957,327

[22] Filed: Oct. 24, 1997

Related U.S. Application Data

[60] Provisional application No. 60/041,192, Mar. 21, 1997.

[51] Int. Cl.⁷ .............................. A61K 9/127; C07H 21/04
[52] U.S. Cl. ............................ 424/450; 436/71; 436/829; 536/23.1; 536/24.5
[58] Field of Search .................... 436/829, 71; 536/23.1, 536/23.31, 24.5; 435/6; 424/450

[56] References Cited

U.S. PATENT DOCUMENTS

| | | | |
|---|---|---|---|
| 5,756,122 | 5/1998 | Thierry et al. | 424/450 |
| 5,827,703 | 10/1998 | Deb et al. | 435/172.3 |

FOREIGN PATENT DOCUMENTS

| | | |
|---|---|---|
| WO 95/11670 | 5/1995 | WIPO. |
| WO 95/32987 | 12/1995 | WIPO. |

OTHER PUBLICATIONS

Maher et al., Specific hybridization arrest of dihydrofolate reductase mRNA in vitro using antisense RNA or antisense oligonucleotides, Archives of Biochemistry and Biophysics, vol. 253 (1), pp. 214–220, Feb. 15, 1987.

*Primary Examiner*—David Guzo
*Assistant Examiner*—Andrew Wang
*Attorney, Agent, or Firm*—Burns, Doane, Swecker & Mathis, LLP

[57] ABSTRACT

It is possible to radiosensitize tumor cells by administration of compositions containing the Human antisense c-raf-1 oligodeoxyribonucleotide (ODN/oligo) sequence: 5'-GTGCTCCATTGATGC-3' (seq. #1) wherein only the end bases are phosphorylated is a preferred embodiment. Antisense sequences of up to 40 bases which containing this sequence may be used in accord with the teachings of this disclosure. Compositions comprising a cationic liposome of dimethyldioctadecyl ammonium bromide, phosphatidylcholine and cholesterol may be used as a carrier system. The liposomes provide a new carrier system that is particularly useful for administration of sequences for therapy.

13 Claims, No Drawings

SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
      (A) LENGTH: 15 base pairs
      (B) TYPE: nucleic acid
      (C) STRANDEDNESS: single
      (D) TOPOLOGY: unknown (ii) MOLECULE TYPE: DNA (genomic)

(iii) HYPOTHETICAL: NO (iv) ANTI-SENSE: YES (xi) SEQUENCE DESCRIPTION: SEQ ID NO:1:

GTGCTCCATT GATGC        15

(2) INFORMATION FOR SEQ ID NO:2:

(i) SEQUENCE CHARACTERISTICS:
      (A) LENGTH: 25 base pairs
      (B) TYPE: nucleic acid -continued

```
        (C) STRANDEDNESS: single
        (D) TOPOLOGY: unknown (ii) MOLECULE TYPE: DNA (genomic)

(iii) HYPOTHETICAL: NO (iv) ANTI-SENSE: YES (xi) SEQUENCE DESCRIPTION: SEQ ID NO:2:

CCTGTATGTG CTCCATTGAT GCAGC                                                    25

(2) INFORMATION FOR SEQ ID NO:3:

(i) SEQUENCE CHARACTERISTICS:
         (A) LENGTH: 15 base pairs
         (B) TYPE: nucleic acid
         (C) STRANDEDNESS: single
         (D) TOPOLOGY: unknown (ii) MOLECULE TYPE: DNA (genomic)

(iii) HYPOTHETICAL: NO (iv) ANTI-SENSE: YES (xi) SEQUENCE DESCRIPTION: SEQ ID NO:3:

GCATCAATGG AGCAC                                                               15
```

LIPOSOMES CONTAINING OLIGONUCLEOTIDES

This application takes priority from Provisional application Ser. No. 60/041,192 filed Mar. 21, 1997. This work was supported by grants from the National Institutes of Health. The United States Government has certain rights in this invention.

FIELD OF THE INVENTION

This invention is related to use antisense of sequences of ≦40 bases for enhancing radiosensitivity of radiation-resistant tumors and to cationic liposomes which are particularly useful as carriers for antisense sequences.

BACKGROUND OF THE INVENTION

Radiation therapy is an important treatment modality of cancer. However, therapeutic management may be limited by the inherent relative resistance of some cancers to the cytotoxic effects of ionizing radiation. Recently, several lines of investigation have coalesced to demonstrate a link between certain oncogenes (ras, raf, cot, mos, myc), growth factors (PDGF, FGF) and the phenomenon of cellular resistance to ionizing radiation.

It was previously reported that expression of antisense c-raf-1 cDNA results in reduced expression (RNA) of c-raf-1 gene, a cause of delayed tumor growth in athymic mice and in enhanced radiation sensitivity of relatively radioresistant laryngeal squamous carcinoma cells, SQ-20B (Kasid et al., Science 243:1354–1356, 1989).

SUMMARY OF THE INVENTION

It is possible to radiosensitize tumor cells by administration of compositions containing the Human antisense c-raf-1 oligodeoxyribonucleotide (ODN/oligo) sequence:
5'-GTGCTCCATTGATGC-3' (seq. #1) wherein only the end bases are phosphorylated is a preferred sequence. Antisense sequences of up to 40 bases which containing this sequence may be used in accord with the teachings of this disclosure. A composition of the 25-mer oligo:
5'-CCTGTATGTGCTCCATTGATGCAGC-3' (seq. #2) wherein the sequence is also effective. Compositions comprising cationic liposomes containing at least one non-toxic cationic lipid, phosphatidycholine and cholesterol may be used as a carrier system.

DESCRIPTION OF THE INVENTION

The search for clinically useful radiation sensitizers for treatment of cancers which fail to respond to radiation therapy has been actively pursued. This invention provides specific sequences which, while inducing radiation sensitivity on tumor cells, is non-toxic to normal tissue. As little as 10 pmol/μl of the sequences encapsulated in liposomes is effective when tumor cells are contacted with the compositions. It was found that the expression and enzymatic activity of Raf-1 protein are inhibited in cells exposed to raf antisense oligodeoxyribonucleotide (As-ODNs) directed against the translation initiation site of human c-raf-1 cDNA. In contrast, treatment of cells with an equimolar concentration of raf sense oligodeoxyribonucleotide (S-ODNs) had no effect on the expression and activity of Raf-1. Furthermore, it was observed radiosensitization of raf As-ODNs-treated SQ-20B cells. The dose modifying factor of As-ODNs treatment was ~1.4. This demonstrates that raf As-ODNs is a DNA sequence-specific radiosensitizer which may have potential for use in the radiation therapy of cancers. Hence, the method of the invention comprises administration of a radiosensitizing effective amount of at least one antisense nucleotide of no more than 40 bases containing the sequence 5'-GTGCTCCATTGATGC-3' (SEQ ID NO: 1).

This invention provides new liposomal compositions which provide means of enhancing the effect of oligonucleotides encapsulated in the novel liposomes. The invention is exemplified using encapsulated raf oligodeoxyribonucleotides. The novel cationic liposomes of the invention were prepared using dimethyldioctadecyl ammonium bromide, phosphatidylcholine and cholesterol. However, other non-toxic cationic lipids such as N-(2,3-(dioleoyloxy)propyl)-N,N,N-trimethyl ammonium chloride or 1-[2-(9(Z)-octadecenoyloxy)-ethyl]-2-(8(Z)heptadecenyl)-3-(2-hydroxyethyl)-imidazolinium chloride may be used. These liposomes provide protection from degradation in plasma and normal tissues to protect the oligonucleotides while they are reaching their intended target cells. Hence, smaller amounts of oligonucleotides are needed to obtain desired results.

Cationic liposomes have been used to deliver genes in vitro and in vivo (Felgner, Editorial, Human Gene Therapy 7:1791–1793, 1996). The novel formulation of the cationic liposomes to encapsulate antisense raf oligonucleotides has been tested and found effective. It has been found that these liposomes encapsulate >90% oligos. Liposomal encapsulation provides protection of antisense raf oligonucleotide from degradation in plasma, and normal tissues, and that tumor cells treated with the liposome-encapsulated antisense raf oligo (LE-ATG-AS raf ODN) are significantly radiosensitive compared to control or sense raf oligo-treated cells. It is now disclosed herein that LE-ATG-AS raf ODN inhibits Raf-1 protein expression in solid tumors. (Gokhale et al., "Antisense 97: Targeting the Molecular Basis of Disease," Cambridge Symposium Meeting, May 1997). The liposomal compositions of the invention disclosed herein are believed to be particularly useful as radiosensitizers in solid tumors.

Materials and Methods

Oligodeoxyribonucleotides

The sense and antisense raf ODNs were designed against the translation initiation site of human c-raf-1 cDNA in accord with the teachings of Bonner (Bonner et al., Nucleic Acids Res., 14:1009–1015, 1986), and have the following sequence: sense ODN (ATG-S raf), 5'-GCATCAATGGAGCAC-3' (seq. #3); antisense ODN (ATG-AS raf), 5'-GTGCTCCATTGATGC-3' (seq. #1), Only two of the bases, one at each end, are phosphorothioated. While antisense sequences of raf of up to 40 bases containing seq. #1 may be used, the larger sequences may be less effective. The fully phosphorothioated sequences may also be effective, but are more likely to cause toxic effects. That the sequences having only the end bases phosphorothioated are non-toxic to normal cells greatly enhances the value of such sequences for use in targeting malignant cells.

Synthesis and Purification of ODNs

Oligodeoxyribonucleotide synthesis was performed at Lofstrand Labs Limited, Gaithersburg, using Beta-Cyanoethyl Phosphoramidite chemistry on Biosearch 8750 DNA synthesizers. Desired base linkages were modified to phosphorothioate groups using 3H-1,2-benzodithiole-3-1,1,1-dioxide as the sulfurizing agent. Oligos synthesized at the 15 μmol scale were cleaved and deprotected in 30% ammonium hydroxide for 24 hours at room temperature and purified over reverse phase chromatography columns. Deprotected DMT-On (trytl on) oligos retained by the support column as failure sequences were washed off in basic aqueous solution. Full length product was detritylated using 2% trifluoro-acetic acid, washed with sterile, deionized water and eluted with 20% acetonitrile, dried and resuspended in sterile, deionized water. For quality control, a small aliquot of each oligo preparation was $^{32}$P-end labeled and visualized by polyacrylamide gel electrophoresis (20% acrylamide and 5% bis) followed by densitometer scanning of the labeled products.

Source of Cells

The SQ-20B tumor cells used were established in culture from the laryngeal squamous carcinoma of a patient who had failed a full course of radiation therapy. In vitro radiation survival analysis has confirmed that these tumor cells are relatively radioresistant. Previously, it had been demonstrated that the transfection of antisense human c-raf-1 CDNA into SQ-20B cells leads to the down-regulation of endogenous raf-1 gene expression, delayed tumor growth in athymic mice, and enhanced radiation sensitivity compared with the sense c-raf-1 cDNA transfectants, and the untransfected tumor cells. Hence a "dual" role was proposed for Raf-1 in these tumor cells; a direct role in the expression of the malignant phenotype, and an indirect role in cellular responses to radiation damage.

Cell Culture, Cell Viability and Cell Cycle Assay

SQ-20B stock cultures were grown and maintained in complete Dulbecco's modified MEM (GIBCO/BRL) containing 20% heat inactivated fetal bovine serum (FBS), 2 mM glutamine, 0.1 mM non-essential amino acids, 0.4 μg/ml hydrocortisone, 100 μg/ml streptomycin and, 100 U/ml penicillin. For cell viability and cell cycle analysis, logarithmically growing cells were cultured in T-25 flasks, complete medium was replaced with 1% FBS containing medium in the presence of a desired concentration of ODNs followed by continued incubation for various times. Control cells were grown in 1% FBS containing medium without ODNs. Cells were collected by trypsinization and viability was determined by the trypan blue dye exclusion assay. Duplicate samples were analyzed by the FACS method to determine the % distribution of cells in different phases of the cell cycle.

Intracellular Uptake and Stability of ODNs

Stock solutions of oligos were prepared by reconstitution of the lyophilized compounds in sterile phosphate buffered saline (PBS) just before use. Oligos (10 pmol/μl) were 5'-end labeled with [γ-$^{32}$P]ATP (50 μCi, 3000 Curies/mmol) and T4 polynucleotide kinase (10 U/μl), and purified on ChromaSpin-10 column (Clontech). Logarithmically growing cells were rinsed with Hank's balanced salt solution and fresh medium containing 1% FBS, 100 pmol/μl ODNs, and radiolabeled ODNs (2×10$^6$ cpm) was added. Following incubation at 37 °C. in a humidified, 5% CO$_2$ atmosphere for the desired time, cells were collected, washed three times in PBS, and lysed for 2 hours at 37° C in the buffer containing 10 mM Tris-HCl (pH 7.5), 1% SDS, and 200 μg/ml proteinase K. DNA isolation was performed using the phenol:chloroform:isoamyl-alcohol (25:24:1) extraction procedure. ODNs uptake was determined by liquid scintillation counting of the aqueous phase, and was expressed as a percentage of the total radioactivity applied to the cells. Aliquots of the cell extracts (5×10$^3$ cpm per sample) were resuspended in sample buffer (95% formamide, 0.05% xylene cyanol, 0.05% bromophenol blue) and electrophoresed on 8 M Urea-20% polyacrylamide gel. The dried gel was auto-radiographed to visualize the oligos.

Raf-1 Immunoprecipitation, Immunoblotting, and In Vitro Kinase Activity Assays Cells were washed twice with cold PBS and lysed at 4° C. for 10 min. in RIPA buffer (1% Triton X-100, 0.1% SDS, 0.5% sodium deoxycholate, 100 mM NaCl, 1 mM phenylmethylsulfonyl fluoride, 20 μg/ml aprotinin, 20μg/ml leupeptin). Insoluble material was removed by centrifugation at 4° C. for 30 min at 9,000 xg and protein concentration was determined (Pierce). Immunoprecipitation was performed by incubating the lysate with polyclonal Raf-1 antibody directed against the last 12 amino acids of human Raf-1 and conjugated with Protein A-Agarose (Santa Cruz). Immunoprecipitates were washed once with the lysis buffer, twice with 0.5 M LiCl-0.1 M Tris (pH7.4), and once with 10 mM Tris (pH 7.4). For immunoblotting, the immunecomplex was boiled in Lammeli sample buffer and electrophoresed on a 7.5% SDS-poly-acrylamide gel, followed by western blotting using Raf-1 antibody and detection of Raf-1 protein by the ECL method according to the manufacturer's protocol (Amersham). Raf-1 protein kinase activity was determined in vitro using a pseudosubstrate peptide (Syntide 2, Santa Cruz) as substrate. The phosphotransferase assay was performed by incubating Raf-1 immunoprecipitates along with the exogenous substrate for 20 min at 30° C. in 40 μl of reaction buffer containing 25 mM HEPES (pH7.4), 25 mM β glycerol phosphate, 1 mM DTT, 10 mM MnCl$_2$, 100 μM ATP, and 10 μCi of [γ-$^{32}$P]ATP. The assay was terminated by spotting 20 μl of the reaction mix onto 2 cm×3 cm pieces of Whatman P81 phospho-cellulose paper. The filters were washed four times for 15 min in a solution of 0.85% phosphoric acid. The Syntide 2-associated $^{32}$P radioactivity bound to the filters was quantitated by Cerenkov counting.

Clonogenic Radiation Survival Assay, and Data Analysis

The appropriate number of tumor cells were seeded into T-25 flasks in complete medium containing 20% FBS. Cells were allowed to attach for 8 hr and the medium was replaced with medium containing 1% FBS and 100 pmol/μl of raf S- or As-ODNs. Control cells were incubated with complete medium containing 1% FBS. oligo treatment lasted for 10 hr, followed by exposure of the cells to the indicated graded doses of γ-radiation. Irradiations were performed using a $^{137}$Cs gamma irradiator (J L Shepard MARK I irradiator) at a dose rate of 3.83 Gy/min. The irradiated cells were then maintained under these incubation conditions for an additional 2 hr. The growth medium in all flasks then was replaced with complete medium containing 20% FBS and the cells were incubated for 7–10 days. Surviving colonies were fixed and stained with 1% methylene blue. Colonies greater than 50 cells were scored and the data were fitted to the Albright's computer-generated single-hit multitarget and linear-quadratic models of radiation survival response.

Liposome Preparation

Liposome-encapsulated raf oligodeoxyribonucleotides, LE-ATG-S raf ODN and LE-ATG-AS raf ODN, were prepared using dimethyldioctadecyl ammonium bromide, phosphatidylcholine and cholesterol (Avanti Polar Lipids, Inc., Alabaster, Ala., USA) in a molar ratio of 1:3.2:1.6. Briefly, the lipids dissolved in chloroform or methanol were evaporated to dryness in a round-bottomed flask using a rotatory vacuum evaporator. The dried lipid film was hydrated overnight at 4° C. by adding 1 ml of ODN at 1.0 mg/ml in phosphate buffered saline (PBS). The film was dispersed by vigorous vortexing and the liposome suspension was sonicated for 5 min in a bath type sonicator (Laboratory Supplies Co. Inc., Hicksville, N.Y., USA). The ODN to lipid ratio was 30 μg ODN/mg of lipid. The unencapsulated ODN was removed by washing the liposomes by centrifugation (3 times at 75,000 g for 30 min) in PBS. The encapsulation efficiency was determined by the scintillation counting of an aliquot of the preparation in which traces of $^{32}$P-end labeled ODN were added to the initial ODN. The entrapment efficiency was found to be >90% (n=10). The liposome encapsulated ODN were stored at $_4$° C. and used within 2 weeks of preparation. Blank liposomes were prepared exactly as described above but without ODN.

Animals

Male Balb/c nu/nu mice, 10–12 weeks old, were maintained in the RRF facility of the Georgetown University according to accredited procedure and fed purina chow and water ad libi tum.

Pharmacological Disposition Studies

The pharmacological disposition of free (ATG-AS) or liposome-encapsulated antisense raf oligodeoxyribonucleotide (LE-ATG-AS) was carried out in Balb/c nu/nu mice. Male Balb/c nu/nu mice were injected intravenously via tail vein with 30 mg/kg of ATG-AS raf ODN or LE-ATG-AS raf ODN. At 5 min, 15 min, 30 min, 1 h, 2 h, 4 h, 8 h, 24 h and 48 h after injection, one animal in each group was bled from the retro-orbital sinus into heparinized tubes and sacrificed by cervical dislocation. The blood was centrifuged immediately at 2000 r.p.m for 10 min at 4° C. to separate the plasma. The liver, spleen, kidney, heart and lung were rapidly excised and rinsed in ice-cold normal saline. The organs and plasma were stored frozen at −70° C. until analysis.

ODN was isolated from plasma samples using the phenol/chloroform extraction method, and from tissues using a DNA extraction kit (Stratagene, La Jolla, Calif., USA). The extracts were then loaded onto 20% polyacrylamide/8 M urea gels and electrophoresed in TBE buffer. The gel was electroblotted onto nylon membrane in 0.5× TBE buffer at 20 V for 1 h. The blots were probed with $^{32}$P-labeled sense raf ODN (ATG-S raf ODN) in Quickhyb buffer (Stratagene, La Jolla, Calif., USA) at 30° C. overnight. The ODN concentration standard was prepared by spiking known amount of the ATG-AS raf ODN in blank plasma or blank tissue samples, followed by extraction as described above. The autoradiographs were scanned using a computer program (ImageQuant software version 3.3, Molecular Dynamics), and the amounts of ATG-AS raf ODN in various samples were calculated by comparison to standards.

SQ-20B Tumor Xenograft Studies

Logarithmically growing SQ-20B cells (2×10⁶) were injected subcutaneously in the flank region on both sides in male Balb/c nu/nu mice under mild anesthesia. Tumors were allowed to grow to a mean tumor volume of 115 mm³ before initiation of ODN treatment.

For intratumoral delivery of LE-ATG-AS raf ODN or LE-ATG-S raf ODN, mice were randomly divided into 3 groups. Three mice in each group received intratumoral injections of 4 mg/kg LE-ATG-AS raf ODN on the right flank, and LE-ATG-S raf ODN on the left flank. The ODN was administered intratumorally daily for 7 days. Control groups received normal saline or blank liposomes. Mice were sacrificed 24 hours after the last dose of ODN, and the organs were rapidly excised, rinsed in ice-cold normal saline and stored at −70° C. until analysis. Raf-1 protein expression was analyzed from tissue homogenates by immunoprecipitation and immunoblotting and quantified using the ImageQuant computer program as described above.

Results

Effects of Raf ODNs on Cell Viability and Cell Cycle Distribution, and Intracellular Uptake ODNs sequences were directed towards the translation initiation site of human c-raf-1 cDNA (15-mer, ends-phosphorothioated, S/As; 25-mer, fully-phosphorothioated, S-F/As-F). Since cell survival in response to γ-radiation is regulated during the cell cycle, and since several reports have suggested the possibility of a cell cycle control of Raf-1 protein kinase activity, it was important to first determine the effects of As-ODNs on the cell cycle distribution pattern of SQ-20B cells. Logarithmically growing cells were exposed to 25–100 pmol/μl of various ODNs for 4–12 hr, and the cell viability and cell cycle distribution patterns were measured. Sense and antisense ODNs showed toxicity as compared to the control cells in 1% FBS-medium without oligos. The cell cycle distributions of ODNs-treated cells were also found to differ as compared to control cells. These data are in general agreement with previous reports suggesting non-specific effects due to the introduction of oligos per se. Remarkably, ends-modified As-ODNs was neither cytotoxic nor had any significant effect on the cell cycle distribution profile of SQ-20B cells as compared to sense ODNs (S-ODNs). Similar observations were made with As-F and S-F ODNs. The intracellular uptakes of ODNs were examined. A linear increase in the intracellular level of ODNs was seen at between 2–12 hr post-treatment. Approximately 4% (equivalent to 4 pmol/μl) of the total extracellular or applied ODNs was taken up by these tumor cells by 12 hr. Intracellular ODNs were also found to be stable as 15-mers.

Specificity of Inhibition of Raf-1

To ascertain the specificity of inhibition of Raf-1 protein kinase by raf As-ODNs, all experiments were performed, in parallel, using two controls: i) cells were exposed to raf S-ODNs using treatment conditions identical to As-ODNs to rule out the influence of non-specific effects due to ODNs; and ii) control cells were treated with 1% FBS containing medium (without ODNs) to determine the base-line levels of the Raf-1 expression and enzymatic activity in SQ-20B cells.

The dose-dependence and time-course of inhibition of Raf-1 protein expression by As-ODNs was studied using a combination of Raf-1 immunoprecipitation and immunoblotting assays. Densitometric analysis of the Raf-1 band (~75 kDa) showed that about 40% inhibition of Raf-1 protein expression occurred at 12 hr when 100 pmol/μl As-ODNs was applied to the cells. Raf-1 protein expression in the S-ODNs-treated cells (extracellular 100 pmol/μl, 12 hr) was found to be identical to the expression in untreated control cells, and in cells exposed to 25 pmol/μl extracellular As-ODNs. Specificity of the Raf-1 antibody was confirmed by elimination of the ~75 kDa band observed in control cells when immunoprecipitation was performed with antigen-blocked antibody. Time-course experiments revealed that approximately 50% inhibition of Raf-1 protein was achieved by 12 hr post-incubation with 100 pmol/μl extracellular As-ODNs. The inhibitory effect of As-ODNs appeared to diminish by 18 hr. This recovery of the Raf-1 expression may be attributed to the apparent degradation of As-ODNs over time and to the synthesis of new protein. Nevertheless, three independent studies indicated that approximately 50% inhibition of Raf-1 protein occurred by 12 hr in the As-ODNs-treated cells as compared to cells treated with equimolar concentration of S-ODNs.

Having established 100 pmol/μl as a non-toxic and inhibitory extracellular dose of raf As-ODNs in SQ-20B cells relative to the equimolar concentration of S-ODNs, the effect of As-ODNs on in vitro phosphotransferase activity of Raf-1 protein kinase was examined. Consistent with immunoblotting data, approximately 50% inhibition of the in vitro Raf-1 protein kinase activity was noted in Raf-1 immunoprecipitates of As-ODNs-treated cells as compared to the S-ODNs-treated cells (applied ODNS: 100 pmol/μl, 12 hours) and the untreated control cells. Experiments were also performed to measure the Raf-1 immune-complex-associated in vitro kinase activity in tumor cells exposed to the fully modified ODNs (S-F/As-F, applied dose 100 pmol/μl, 12 hr). Inhibition of Raf-1 activity was observed in the As-F ODNs-treated cells as compared to the S-F ODNs response. It is noteworthy that the expression and activity of Raf-1 were observed to be similar in the control (C, without oligo) and raf S-ODNs-treated cells (S). This finding along with the concurrent inhibition of the expression and activity of Raf-1 noted in the raf As-ODNs-treated cells (As), implied that the inhibition of Raf-1 protein kinase was sequence-specific, and not due to the non-specific effects of ODNs.

Raf As-ODNs is a Biologic Radiosensitizer of SQ-20B Cells

Radiation survival dose responses of SQ-20B cells exposed to S-and As-ODNs (100 pmol/μl, 12 hr) were evaluated. (S- and As-ODNs used in this study do not contain the G-quartet or CpG motifs previously shown to be responsible for non-antisense-specific effects such as enhanced affinity for protein or interference with the immune response.) The plating efficiencies indicated that the As-ODNs treatment had no effect on cell viability as compared to S-ODNs-treated cells (Table 1). These data are also in agreement with the S- and As-ODNs effects on the viability of logarithmically growing cells discussed earlier. Radiation survival dose responses of the control (without oligo) and S-ODNs-treated cells were almost identical. Most important, As-ODNs treatment resulted in decreases of the shoulder and the slope of the survival curve. The radiobiological parameters were obtained by fitting the data (surviving number of colonies) to the single-hit multitarget ($D_0$, $D_q$, n) and linear-quadratic ($\alpha$, $\beta$) models of radiation survival response. In addition, the value of a model-free parameter, mean inactivation dose (D) was calculated (14) (Table 1). Based on a ratio of the mean inactivation dose, the dose modifying factor (DMF) of As-ODNs treatment was ~1.4. Significant decreases observed in the values of radiobiological parameters, D, $D_q$, and $D_0$ of SQ-20B cells following treatment with the raf As-ODNs indicate a good correlation between the DNA sequence-specific inhibition of Raf-1 protein kinase and the radiosensitization of these relatively radioresistant tumor cells.

The studies indicated that greater than 50% inhibition of Raf-1 expression could be achieved with only 10 pmol.μl of the liposome-encapsulated raf As-ODNs.

Liposomal Encapsulation Protects ATG-AS Raf ODN In Vivo

The plasma concentration-time profile of LE-ATG-AS raf ODN was studied. Dosage of 30 mg/kg LE-ATG-AS raf ODN or ATG-AS raf ODN was administered i.v. in Balb/c nu/nu mice. Blood samples were collected from retro-orbital sinus at indicated times after injection and the ODN in plasma samples was extracted by phenol:chloroform. The samples were electrophoresed on 20% polyacrylamide/8 M urea gel and electroblotted on nylon membrane. The blots were probed with $^{32}$P-labeled ATG-S raf ODN. Autoradiographs were scanned using a computer program (ImageQuant software version 3.3, Molecular Dynamics). St, standard prepared by spiking known concentration of ATG-AS raf ODN in blank plasma. Quantification data were calculated based on a known concentration of the standard sample, and then normalized against dilution factors at various time points.

Following intravenous administration, the peak plasma concentration of 6.39 μg/ml was achieved and intact ODN could be detected up to 24 h. The decrease in plasma concentration of LE-ATG-AS raf ODN followed a biexponential pattern with an initial half-life ($t_{1/1a}$) of 24.5 min and a terminal half-life ($t_{1/2B}$) of 11.36 h. The area under the plasma concentration-time curve for LE-ATG-AS raf ODN was 5.99 μg.h/ml, with total body clearance of 75.94 ml/min/kg and volume of distribution of 74.67 L/kg. In contrast, intact free ODN (ATG-AS raf ODN) was detectable only at 5 min; the plasma concentration being 9.75 μg/ml. These observations indicate that ATG-AS ODN was either rapidly cleared from the circulation, or extensively degraded in plasma due to nuclease activity.

Normal tissue distribution profiles of LE-ATG-AS raf ODN were studied. Tissue samples were collected at indicated times after i.v. administration of 30 mg/kg LE-ATG-AS raf ODN. ODN was extracted from homogenized tissues using a DNA extraction kit (Stratagene). Samples were electrophoresed and electroblotted. The blots were probed with $^{32}$P-labeled ATG-S raf ODN and autoradiographs were analyzed. Quantification data were calculated based on a known concentration of the standard sample, and then normalized against the weight of the tissue sample collected.

Intact ODN could be detected in all organs examined up to 48 hours after administration. Interestingly, following ATG-AS raf ODN administration, intact ODN could be detected only at 5 minutes post-administration in all the organs examined and degradation products were observed at all other times. These findings, along with the plasma data for LE-ATG-AS raf ODN, suggests that ODN with only the end bases phosphorothioated is rapidly degraded in vivo and that liposome encapsulation using the liposomes of the invention protects it from degradation for at least 48 hours.

TABLE 1

Radiation survival parameters of SQ-20B cells treated with raf oligodeoxyribonucleotides

| raf ODNs | No. of Expts. | $D_o$ (Gy) | $D_q$ (Gy) | n | $\alpha$ (Gy$^{-1}$) | $\beta$ (Gy$^{-2}$) | D (Gy) |
|---|---|---|---|---|---|---|---|
| Sense/Control* | 6 | 3.028 | 1.265 | 1.519 | 0.2373 | 0.0050 | 3.694 |
| Antisense | 3 | 2.374 | 0.551 | 1.261 | 0.3614 | 0.0038 | 2.628 |

The appropriate number of cells were seeded into two replica T-25 flasks per dose in each experiment. Control cells were cultured in medium containing 1% FBS without oligo.

Plating efficiencies of the S-ODNs-treated, As-ODNs-treated and control cells were in the range of 13–58%, 28–61% and 41–67%, respectively. Clonogenic survival data were computer-fitted to the single-hit multitarget and the linear-quadratic models of radiation survival dose response.

Specificity of Inhibition of Raf-1 Protein Expression and Activity In Vitro

Initially, the possibility of cytotoxic effects of liposomes in SQ-20B cells was examined. Blank liposomes, at concentration equivalent to 10 μM LE-ATG-AS raf ODN, were found to be non-cytotoxic as determined by the clonogenic and trypan blue dye exclusion methods. However, blank liposomes showed cytotoxicity at doses higher than 20 μM. Therefore, a dose of 10 μM or less was used for in vitro experiments. Further, 10 μM LE-ATG-AS raf ODN or LE-ATG-S raf ODN was non-toxic to SQ-20B cells.

Specificity of inhibition of Raf-1 protein expression by LE-ATG-AS raf ODN. Logarithmically growing SQ-20B cells were treated with 10 AM LE-ATG-AS raf ODN (AS), 10 μM LE-ATG-S raf ODN (S) or blank liposomes (BL) for indicated time in 1% FBS containing medium. Untreated control cells (C) were simultaneously switched to 1% FBS containing medium for 8 hours. Whole cell lyates were normalized for total protein content and immunoprecipitated with agarose-conjugated polyclonal anti-Raf-1 antibody (Santa Cruz). Immune-complexes were resolved on 7.5% SDS-PAGE and Raf-1 protein expression was detected by immuno-blotting with polyclonal anti-Raf-1 antibody (Santa Cruz), followed by the ECL detection protocol (Amersham). Results from three independent experiments were quantified using a computer program (ImageQuant, Molecular Dynamics), and data are expressed relative to the level of Raf-1 in LE-ATG-S raf ODN-treated cells (bottom). Panel B: Dose-response analysis. Logarithmically growing SQ-20B tumor cells were treated with indicated concentrations of LE-ATG-AS raf ODN (AS) or LE-ATG-S raf ODN (S) in 1% FBS containing medium for 8 h. Normalized cell lysates were analyzed for Raf-1 protein expression.

Logarithmically growing SQ-20B cells were treated with 10 μM LE-ATG-AS raf ODN (AS), or 10 μM LE-ATG-S raf ODN (S) for 8 h in 1% FBS containing medium. Control cells (C) were simultaneously switched to 1% FBS containing medium for 8 hours. Whole cell lysates were normalized for protein content, and Raf-1 was immunoprecipitated. Phosphotransferase activity of Raf-1 in immune-complexes was assayed in vitro using a physiologic substrate MKK1. Radiolabeled reaction products were separated by electrophoresis and autoradiographed.

Time-course experiments revealed that a maximum inhibition (52.3±5.7%) of Raf-1 protein expression (~74kDa) occurred at 8 hours post-incubation of cells with 10 μM LE-ATG-AS raf ODN. The inhibitory effect of LE-ATG-AS raf ODN was maintained up to 24 h (45.6±9.8%). The level of Raf-1 protein was comparable in the control untreated cells (C), blank liposome-treated cells (BL), and LE-ATG-S ODN-treated cells, indicating the LE-ATG-AS raf ODN specifically inhibited the Raf-1 protein expression in SQ-20B cells. Dose response studies showed that 35.94±16.8% and 52.3±5.7% inhibition of Raf-1 expression occurred with 5 μM and 10 μM LE-ATG-AS raf ODN treatment for 8 hours.

The effects of LE-ATG-AS raf ODN on the enzymatic activity of Raf-1 protein kinase using mitogen-activated protein kinase kinase (MKK1) as substrate were studied. In concurrence with Raf-1 protein inhibition data, it was found that 10 μM LE-ATG-AS raf ODN treatment for 8 hours inhibited 62.6±9.0% in vitro phosphotransferase activity of Raf-1 protein. LE-ATG-S raf ODN did not have any effect on the Raf-1 protein kinase activity as compared with the untreated control cells.

LE-ATG-AS Raf ODN is a Biological Radiosensitizer

Radiation survival dose responses of SQ-20B cells exposed to LE-ATG-AS raf ODN, LE-ATG-S raf ODN, and blank liposomes are presented in Table 2. Comparison of the radiation survival dose response of SQ-20B cells treated with LE-ATG-AS raf ODN (AS), LE-ATG-S raf ODN (S), or blank liposomes (BL). The appropriate number of cells were seeded in duplicate to obtain 40–60 colonies per T-25 flask (Costar) for each radiation dose. The clonogenic survival data were computer-fitted to the single-hit multitarget model of radiation survival dose response. Representative data from one experiment performed for each treatment category were evaluated.

The plating efficiencies of cells treated with S/AS ODN or blank liposomes were comparable (Table 2). Radiation survival dose responses of the blank liposome-treated (BL) and LE-ATG-S raf ODN-treated cells were also comparable. LE-ATG-AS raf ODN treatment resulted in a significant radiosensitization (Table 2). Based on a ratio of the mean inactivation dose, the dose modifying factor (DMF) of LE-ATG-AS raf ODN treatment was ~1.6. Significant decreases observed in the values of radiobiological parameters, $\bar{D}$, $D_q$, and $D_0$ of SQ-20B cells following treatment with the LE-ATG-AS raf ODN indicate a good correlation between the DNA sequence-specific inhibition of Raf-1 protein kinase and the radiosensitization of these relatively radioresistant tumor cells.

LE-ATG-AS Raf ODN is a Specific Inhibitor of Raf-1 Protein Expression in Solid Tumor The effects of intratumoral administration of LE-ATG-AS raf ODN and LE-ATG-S raf ODN on the expression of Raf-1 protein was examined in a SQ-20B tumor xenograft model. Mice with tumors on both flanks received intratumorally LE-ATG-AS raf ODN on the right flank, and LE-ATG-S ODN on the left flank. Results demonstrated a significant inhibition of Raf-1 protein in tumor tissue following treatment with LE-ATG-AS raf ODN compared with LE-ATG-S raf ODN (60.3±6.4%).

Inhibition of Raf-1 Protein Expression by LE-ATG-AS Raf ODN in SQ-20B Tumor Xenografts SQ-20B tumors were established subcutaneously in both hind limbs of nude mice, Balb C nu/nu (mean tumor volume 115 mm$^3$). Each animal then received intratumoral injections of LE-ATG-AS raf ODN (AS) on the right flank and LE-ATG-S raf ODN (S) on the left flank at a dose of 4 mg/kg daily for 7 days. Tumor tissue was excised 24 h after the last treatment, and Raf-1 protein expression in tumor samples was analyzed. ECL images were quantified using a computer program (ImageQuant, Molecular Dynamics), and quantification data from three mice are expressed as the level of Raf-1 protein expression in LE-ATG-AS raf ODN-treated tumors relative to LE-ATG-S raf ODN-treated tumors.

Liposomes prepared in accord with the teachings of the invention are non-toxic both in culture and in animals. While only specific liposomes are disclosed herein, the novel carriers may be used for delivery of a variety of DNA-based compounds for delivery.

TABLE 2

Radiation Survival Parameters of SQ-20B Cells Treated with LE-ATG-S/AS raf ODN

| raf ODN | No. of Expts. | $D_o(Gy)$ | $D_q(Gy)$ | $\bar{n}$ | $\alpha(Gy^{-1})$ | $\beta(Gy^{-2})$ | $\bar{D}(Gy)$ |
|---|---|---|---|---|---|---|---|
| Blank liposomes/ | 5 | 2.795 | 1.445 | 2.012 | 0.2184 | 0.0087 | 3.659 |
| LE-ATG-S* | | ± 0.38 | ± 1.22 | ± 1.34 | ± 0.11 | ± 0.00 | ± 0.02 |
| LE-ATG-AS | 3 | 2.287 | 0.051 | 1.021 | 0.4385 | 0.0000 | 2.280 |
| | | ± 0.23 | ± 0.05 | ± 0.19 | ± 0.05 | ± 0.00 | ± 0.00 |

The appropriate number of cells were seeded in duplicate T25 flasks per dose in each experiment. Plating efficiencies of the blank liposome-treated, LE-ATG-S raf ODN-treated and LE-ATG-S raf ODN-treated cells were in the range of 65–79%, 52–83%, and 59–90% respectively. Clonogenic survival data were computer-fitted to the single-hit multi-target and the linear-quadratic models of radiation survival dose response.

The liposomes of the invention provide significant protection of antisense oligonucleotides against degradation in blood and normal tissue. The formulation may replace the need for complete modification of all bases of the antisense oligonucleotides for therapeutic uses. Compositions comprising oligonucleotides may be administered in many ways, depending on the target tissue.

The particular method used to deliver compositions of the invention to the tissues of the intact animal will depend on the particular tissue to which it is administered. For example, compositions of the invention can be administered intrathecally to facilitate contact of the active agent with neuronal tissue. For administration to the lung, the liposomal compositions may be administered transbronchially as a spray or mist. Liposomal compositions may also be administered to tissue locally during surgery. For example, the compositions could be administered into the peritoneal cavity as a mist during surgery.

The liposomes may also be injected into the target tissue or into the arterial blood supply to the target tissue. When the target tissue is the lining of a hollow organ, they may be introduced into the lumen of the organ.

The dosage required will depend on the agent and the subject being treated with the liposomal compositions. For example, when a radiosensitizing oligonucleotide is administered by means of liposomes, a radiosensitizing amount of oligonucleotides must reach the target organ.

The radiosensitizing oligonucleotides may also be administered systemically. A preferred method of administration is by intravenous injection.

Acceptable carriers include, for example, glucose, saline, phosphate buffered saline. Carriers may also contain other substances frequently found in pharmaceuticals such as preservatives, emulsifiers and surfactants.

Dosage will depend on the extent to which it is possible to present the active agents to the target tissue. The appropriate dosage should deliver a serum concentration of about 1 $\mu$g/ml to 1000 $\mu$g/ml. In some instances, this dosage can be delivered into the target tissue directly. Hence, that level of dosage need not be achieved in the total blood volume.

What we claim is:

1. A composition comprising cationic liposomes which consist essentially of dimethyldioctadecyl ammonium bromide (DDAB), phosphatidylcholine (PC), and cholesterol, and having encapsulated therein at least one oligonucleotide, and further comprising at least one pharmaceutically acceptable carrier.

2. The composition of claim 1, wherein said oligonucleotide is about 15 to 40 nucleotides long.

3. The composition of claim 1, wherein said oligonucleotide is about 15 to 25 nucleotides long.

4,. The composition of claim 1, wherein said oligonucleotide is radiolabeled.

5. The composition of claim 1, wherein said oligonucleotide is an antisense DNA.

6. The composition of claim 1, wherein said oligonucleotide is selected from the group consisting of SEQ. ID. NO: 1, and SED. ID. NO:2.

7. The composition of claim 1, which provides for the delivery of a serum concentration of about 1 µg/ml to 1,000 µg/ml of said oligonucleotide upon in vivo administration.

8. The composition of claim 1, wherein said pharmaceutically acceptable carrier is selected from the group consisting of glucose, saline, phosphate buffered saline, and said composition further optionally includes at least one preservative, emulsifier or surfactant.

9. The composition of claim 1, which is suitable for in vivo administration.

10. The composition of claim 9, which is administerable by a mode selected from the group consisting of systemic, intrathecal, intratumoral, and transbronchial administration.

11. The composition of claim 1, which is suitable for administration by injection.

12. The composition of claim 1, wherein the respective molar ratios of DDAB, PC and cholesterol are about (1:3.2:1.6).

13. The composition of claim 1, wherein said oligonucleotide is a modified oligonucleotide.

* * * * *